United States Patent
Ozgul et al.

(10) Patent No.: US 8,976,021 B2
(45) Date of Patent: Mar. 10, 2015

(54) REMOTE PATIENT MANAGEMENT DEVICE AND METHOD

(75) Inventors: Mehmet Emin Ozgul, Kocaeli (TR); Emre Tavsancil, Kocaeli (TR); Kamil Erman, Kocaeli (TR)

(73) Assignee: Turkcell Teknoloji Arastirma Ve Gelistirme Anonim Sirketi, Kocaeli (TR)

( * ) Notice: Subject to any disclaimer, the term of this patent is extended or adjusted under 35 U.S.C. 154(b) by 83 days.

(21) Appl. No.: 13/807,649

(22) PCT Filed: Jan. 23, 2012

(86) PCT No.: PCT/IB2012/050301
§ 371 (c)(1),
(2), (4) Date: Dec. 28, 2012

(87) PCT Pub. No.: WO2013/098658
PCT Pub. Date: Jul. 4, 2013

(65) Prior Publication Data
US 2013/0169432 A1    Jul. 4, 2013

(30) Foreign Application Priority Data
Dec. 28, 2011 (TR) ................................ 2011/13126

(51) Int. Cl.
| | |
|---|---|
| G08B 1/08 | (2006.01) |
| G08B 21/02 | (2006.01) |
| G06F 19/00 | (2011.01) |
| A61B 5/00 | (2006.01) |

(52) U.S. Cl.
CPC .......... *G08B 21/02* (2013.01); *G06F 19/3418* (2013.01); *A61B 5/0022* (2013.01); *G06F 19/3412* (2013.01)
USPC .............. 340/539.12; 340/539.11; 340/573.1; 600/309

(58) Field of Classification Search
USPC ................. 340/539.12, 573.1, 539.11, 573.4; 600/300, 309; 370/466
See application file for complete search history.

(56) References Cited

U.S. PATENT DOCUMENTS

| | | | | |
|---|---|---|---|---|
| 8,140,160 | B2 * | 3/2012 | Pless et al. ...................... | 607/31 |
| 8,269,634 | B2 * | 9/2012 | Fischell et al. ............. | 340/573.1 |
| 2010/0049005 | A1 | 2/2010 | Perez et al. | |

FOREIGN PATENT DOCUMENTS

| | | |
|---|---|---|
| WO | WO 02/100262 A1 | 12/2002 |
| WO | WO 2006/108858 A1 | 10/2006 |
| WO | WO 2008/064053 A2 | 5/2008 |

(Continued)

OTHER PUBLICATIONS

International Search Report, mailing date Jun. 14, 2012, for corresponding International Application No. PCT/IB2012/050301.

(Continued)

*Primary Examiner* — Toan N Pham
(74) *Attorney, Agent, or Firm* — Intellectual Property Law Group LLP (57) ABSTRACT

The present invention relates to a remote patient management device (1) and method (1000) which facilitates to particularly follow up chronic diseases and keep them under control and enables to transfer measurement results, which should be made by people with these diseases and transmitted to healthcare personnel properly, in an easy and safe way automatically.

18 Claims, 8 Drawing Sheets

(56) References Cited

FOREIGN PATENT DOCUMENTS

| WO | WO 2008/073584 | A2 | 6/2008 |
| WO | WO 2009/032134 | A2 | 3/2009 |

OTHER PUBLICATIONS

Written Opinion, mailing date Jun. 14, 2012, for corresponding International Application No. PCT/IB2012/050301.

* cited by examiner

REMOTE PATIENT MANAGEMENT DEVICE AND METHOD

CROSS-REFERENCE TO RELATED APPLICATIONS

This application is a U.S. National Phase application, under 35 U.S.C. §371, of International Application no.PCT/IB2012/050301, with an international filing date of Jan. 23, 2012 and claims benefit of Turkey Application no. 2011/13126 filed on Dec. 28, 2011, and which are hereby incorporated by reference for all purposes.

TECHNICAL FIELD

The present invention relates to a remote patient management device and method which facilitates to particularly follow up chronic diseases and keep them under control.

BACKGROUND OF THE INVENTION

Nowadays, healthcare personnel such as nurse, doctor can follow up patient's condition from a distance by means of wire or wireless communication devices. Particularly, patients with chronic diseases can be followed up with remote patient follow-up systems. People with these diseases are enabled to make tests, which are required to be realized, by themselves away from healthcare personnel and it is not necessary anymore for the patient to make effort to go to a health centre by means of these systems. After the patient make the tests required by means of the medical devices owned by him/her, data concerning the test are automatically transmitted to health centres where healthcare personnel are present or medical data centre whereto healthcare personnel can have access.

There are systems which are known in the state of the art and enable to follow up patient's condition from a distance. In addition, in the state of the art there are special software which have bluetooth capacity on thereof and are prepared for mobile devices such as mobile phones whereto software can be installed from outside in order to make contact with medical measuring devices that have bluetooth short-range wireless communication capacity, collect and transmit test measurement results to another information system. However, installation of this software and carrying out bluetooth matches between the mobile device and medical devices include difficulties particularly for patients who are elder, children, with mental disabilities or with a low level of education. Also, it is required that health measurement values can be transferred from medical device to mobile device, mobile device is on and in operation, bluetooth services are available and software collecting data on thereof is in operation as well. Each requirement is supposed to be controlled by the patient before and after measurement because data communication cannot be provided in cases where any of the said requirements is not ensured. Leaving bluetooth services on and the fact that communication software is always in operation increase energy consumption of mobile device. And this is not preferred by patients. In addition to these, keeping bluetooth service continuously on leads to serious security risks in mobile devices in which sensitive personal information can be stored.

In the state of the art, there are also systems which manage medical devices via short-range communication methods and gather data. The said systems are designed as medical data collection devices for general purpose and need complex patient interactions both at the step of start using and regular use. In addition, due to the fact that sizes of the said systems can be large as well these devices have portability problems.

The International patent document no. WO2008/073584 discloses a wireless processing system and method of monitoring a medical device and connecting to a medical device. In an embodiment of the invention which is disclosed in the said International patent document, the system comprises a processor, a medical device transceiver, a patient interface, a data transmission transceiver, a memory that is connected to the processor and storage members. The medical device transceiver enables to receive medical data from a plurality of medical devices wirelessly. Medical data received are transmitted to an intermediate device by means of a data transmission transceiver. The patient interface provided in the system may comprise microphone and speaker in order that the system and the patient are in voice communication.

The United States patent document no. US2010/0049005 discloses a wireless device which enables transmission of medical data. The said device comprises a wireless interface, a processor and a medical equipment interface which enables to make contact with the medical equipment. The processor is in touch with the medical equipment interface and the wireless interface. The protocol adaptation takes place from a protocol of incoming data received at the medical equipment interface to a protocol of data to be transmitted through the wireless interface, or vice versa. The data protocol comprises filtering, gathering, partitioning, prioritizing or discarding the incoming data individually or in group.

SUMMARY OF THE INVENTION

Objective of the invention is to realize a remote patient management device and method which enables people with chronic disease to make their tests on a regular basis and transmission of test measurement values to healthcare personnel reliably.

Another objective of the invention is to realize a remote patient management device and method which can establish a connection with medical devices defined and manage the said devices.

A yet another objective of the invention is to realize a remote patient management device and method which provides information such as time, calibration, etc. and information necessary for operation of medical devices defined to said devices.

A further objective of the invention is to realize a remote patient management device and method which can read results of measurements carried out by medical devices defined.

A yet further objective of the invention is to realize a remote patient management device and method which performs operations with minimum patient interaction.

BRIEF DESCRIPTION OF THE DRAWINGS

The "Remote Patient Management Device and Method" realized to fulfil the objectives of the present invention is shown in the figures attached, in which.

DETAILED DESCRIPTION OF SPECIFIC EMBODIMENTS

The components illustrated in the figures are individually numbered, where the numbers refer to the following:
1. Remote patient management device
2. Body
3. Visual unit
4. Sound generating unit
5. Input unit
6. Short-range communication module
7. Long-range communication module
8. Control module
9. Adaptation layer
10. Application
11. Processor
12. Medical device library
13. Update unit
14. Non-volatile memory
1000. Remote patient management method Throughout the description, devices which make tests of patients as medical device, are portable or non-portable, get test results and can connect to the remote patient management device (1) via any wireless communication protocol are disclosed. A server where the remote patient management device (1) transmits the results of the test measurement received from the medical device, information about the remote patient management device (1) and the medical devices are present, and can connect to the remote patient management device (1) via any wireless communication protocol is mentioned as a remote server.

Figure 1:
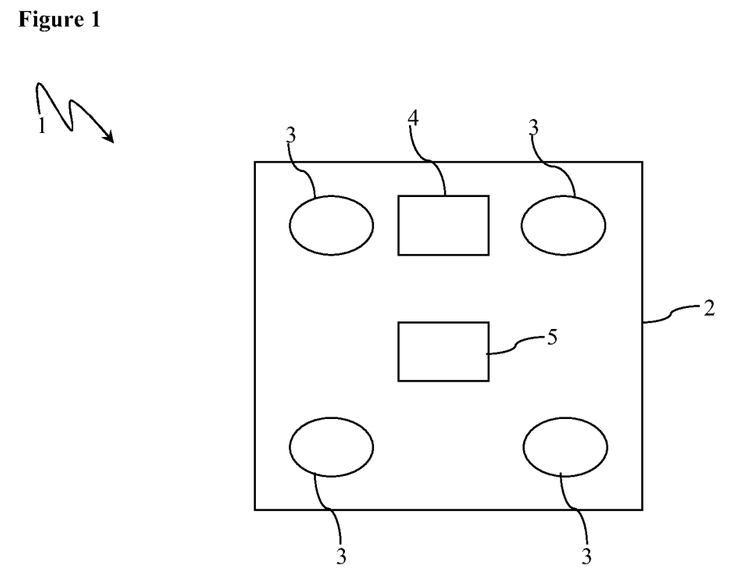
FIG. 1 is a schematic view of the inventive remote patient management device.

The inventive remote patient management device (1) comprises:
a body (2);
a plurality of visual units (3) which are located on the body (2) and enable to inform and warn the patient visually;
at least one sound generating unit (4) which is located on the body (2) and enables to warn and inform the patient vocally;
at least one input unit (5) which is located on the body (2) and enables the patient to carry out input processes;
at least one short-range communication module (6) which is located in the body (2) and comprises at least one interface enabling to get in contact with devices that are present at short-range such as medical devices that will make tests of the patient;
at least one long-range communication module (7) which is located in the body (2) and comprises at least one interface enabling to get in contact with remote servers such as transmitting test measurement results of the patient to healthcare centers;
at least one control module (8) which enables the visual unit (3), the sound generating unit (4) and the input unit (5) to fulfil their duties and to carry out short communication by means of the short-range communication module (6) and remote communication by means of the long-range communication module (7).

Figure 2:
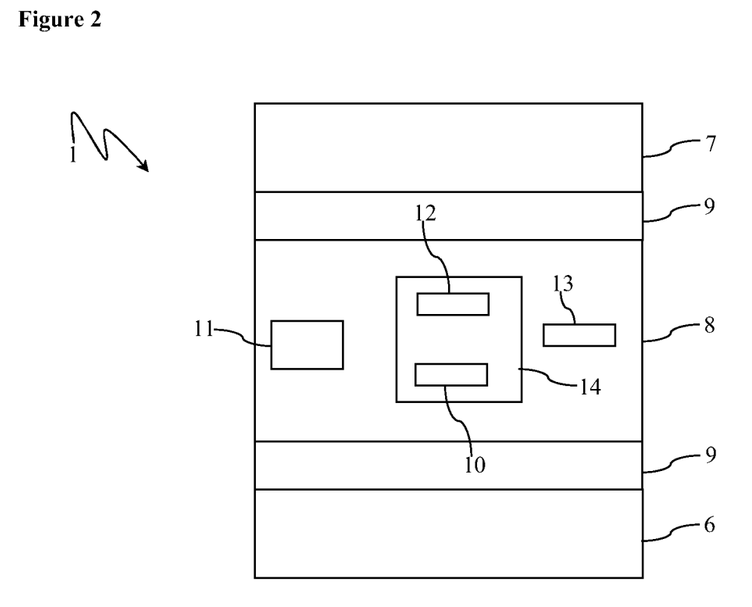
FIG. 2 is a schematic view of architecture of the inventive remote patient management device.

The inventive remote patient management device (1) also comprises at least two adaptation layers (9) which enable the control module (8) to interact with the short-range communication module (6) and the long-range communication module (7) in an isolated manner. The said adaptation layers (9) present a standard set of function, which is necessary for get in contact with medical devices and remote servers, to the control module (8).

The control module (8) involved in the inventive remote patient management device (1) comprises:
at least one application (10) which controls services that enable remote management of the device (1) and updates, and all components;
at least one processor (11) which enables to run the application (10);
at least one medical device library (12) in which identity information relating to the medical devices connected, treatment information and necessary operating information are included;
at least one update unit (13) which enables to control retrieval of information relating to the application (10) or the medical devices connected from remote server; and
at least one non-volatile memory (14) in which the application (10) and the medical device library (12) are kept confidential.

With the visual unit (3) provided in the inventive remote patient management device (1), the patient is enabled to be informed about the operations carried out by the device (1). While the device (1) is performing a process in the event that an error occurs in the process, the visual unit (3) ensures that the patient is warned about the error in the process in a luminous way. In addition, the visual unit (3) enables to inform the patient that the process is concluded successfully in a luminous way as a result of the device (1) performing a process successfully. In a preferred embodiment of the invention, as a result of completion of a process successfully colour of the light emitting from the visual unit (3) and the colour of the light emitting from the visual unit (3) in the event that an error occurs in a process are different so that the patient will not be confused.

With the sound generating unit (4) provided in the inventive remote patient management device (1), the patient is enabled to be informed about operations carried out by the device (1). While the device (1) is performing a process in the event that an error occurs in the process, the sound generating unit (4) ensures that the patient is warned about the error in the process vocally. In addition, the sound generating unit (4) enables to inform the patient that the process is concluded successfully vocally as a result of the device (1) performing a process successfully. In a preferred embodiment of the invention, as a result of completion of a process successfully the tone of the voice coming from the sound generating unit (4) and the tone of the voice coming from the sound generating unit (4) in the event that an error occurs in a process are different so that the user will not be confused.

With the input unit (5) provided in the inventive remote patient management device (1), information of patient relating to processes are enabled to be input to the device (1) manually. For example, information about medical device which will make measurement relating to patient's disease can be input to the device (1) by the patient via the input unit (5) manually. In an embodiment of the invention, keypad is used as the input unit (5). In an alternative embodiment of the invention, touch screen is used as the input unit (5).

The short-range communication module (6) provided in the inventive remote patient management device (1) comprises at least one communication interface which enables the device (1) to get in contact with devices such as medical device located at short-range.

In an embodiment of the invention, the short-range communication module (6) comprises bluetooth communication interface which is defined by IEEE 802.15.1 standard.

In another embodiment of the invention, the short-range communication module (6) also comprises wireless personal networks communication interface which is defined by IEEE 802.15.4 standard.

In yet another embodiment of the invention, the short-range communication module (6) also comprises wireless fidelity (Wi-Fi) communication interface which is defined by IEEE 802.11 series.

In a further embodiment of the invention, the short-range communication module (6) also comprises infrared communication interface.

In a yet further embodiment of the invention, the short-range communication module (6) also comprises wire serial communication interface.

Other than the above-mentioned examples, the short-range communication module (6) also comprises any short-range communication interface which can operate in accordance with the adaptation layer (9) located between the control module (8) and the short-range communication module (6).

The long-range communication module (7) provided in the inventive remote patient management device (1) comprises at least one communication interface which enables the device (1) to get in contact with the servers located at long-range.

In an embodiment of the invention, the long-range communication module (7) comprises communication interface of global system for mobile communications (GSM).

In an embodiment of the invention, the long-range communication module (7) also comprises Ethernet communication interface.

In an embodiment of the invention, the long-range communication module (7) also comprises wireless fidelity (Wi-Fi) communication interface.

Other than the above-mentioned examples, the long-range communication module (7) also comprises any long-range communication interface which can operate in accordance with the adaptation layer (9) located between the control module (8) and the long-range communication module (7).

In the inventive remote patient management device (1), the control module (8) can be activated or deactivated over the adaptation layers (9) of the short-range communication interfaces and long-range communication interfaces which are located inside the short-range communication module (6) and the long-range communication module (7).

In an embodiment of the invention, the long-range communication module (7) comprises at least one subscriber identity module (SIM). By means of the said subscriber identity module, measurement results received from medical devices are transmitted to remote servers such as health centres by being encrypted with certificate keys and encryption methods. Thus, unauthorized access to measurement results from the outside are prevented.

The remote patient management device (1) uses security keys, security certificates and digital signing methods which are provided by the subscriber identity module for secure communication and to store personal health data safely.

In an alternative embodiment of the invention, the inventive remote patient management device (1) comprises a rechargeable battery as power supply. The said battery enables to supply the power needed by the device (1) while the device (1) is performing its duties. In a derivative of this embodiment of the invention, the patient is warned about charging the battery by means of the visual unit (3) and the sound generating unit (4) when the battery charge level drops down below a predetermined level.

The inventive remote patient management device (1) can be available in preferably three different statuses so as to prevent high power consumption. In one of the said statuses, only the visual unit (3) and the sound generating unit (4) can receive energy from the battery, all remaining modules are deprived of energy. This status of the device (1) is called as off-mode. In another one of these statuses, all units in the device (1) can receive power from the battery. However, units are in sleep mode within the period while they are not used but they are in a position where they can be used at any time. This status of the device (1) is called as sleep mode. In another status of the device (1), all units receive energy from the battery. This status of the device (1) is called as operation mode. Due to the off-mode of the device (1), in transportation vehicles such as aircraft it is ensured that the device (1) can be carried without damaging electronic equipment of the transportation vehicle. Due to the sleep mode of the device (1), it is ensured that energy received from battery is reduced while the device (1) is not in operation mode and this provides longer battery life.

Figure 3:
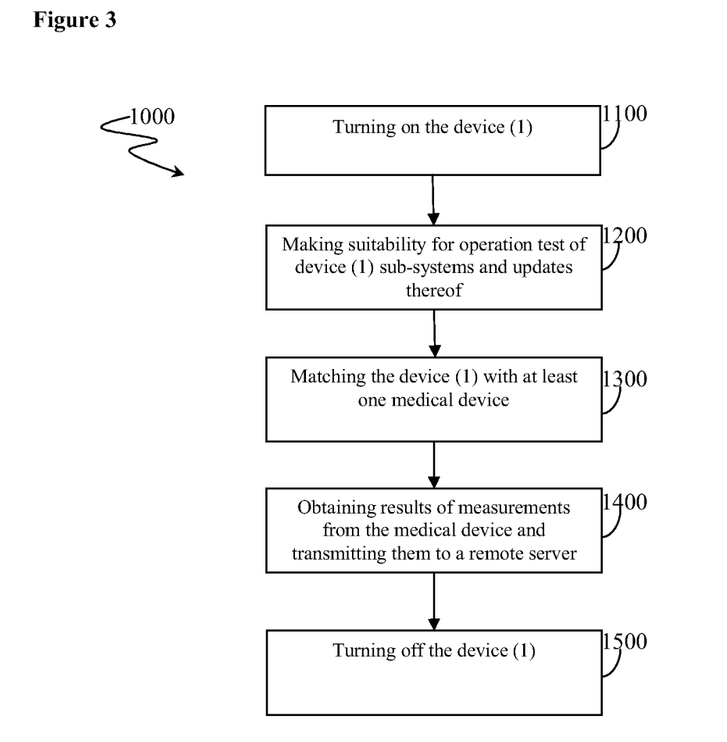
FIG. 3 is a flow diagram regarding the inventive remote patient management method.

The remote patient management method (1000) which enables people with chronic disease to make their tests on a regular basis and transmission of test measurement values to healthcare personnel reliably essentially comprises steps of:
  turning on the device (1) (1100);
  making suitability for operation test of device (1) sub-systems and updates thereof (1200);
  matching the device (1) with at least one medical device (1300);
  obtaining results of measurements from the medical device and transmitting them to a remote server (1400); and
  turning off the device (1) (1500).

In the inventive method (1000), firstly the device (1) is turned on and it is made operable (1100). Upon the device (1) starts operating, the application (10) carries out operation tests in order to determine whether the visual unit (3), the sound generating unit (4), the input unit (5), the short-range communication module (6), the long-range communication module (7) and the adaptation layers (9) of the device (1) operate properly; and enables updates to be loaded from remote servers in the event that there is a new update by interrogating whether there is any update relating to the device (1) (1200). After it is determined that sub-systems of the device (1) are suitable for operation and existing updates are loaded (1200), the device (1) is matched with medical device or devices enabling the patient to make measurements required for his/her health (1300). Subsequent to the matching process (1300), medical devices transfer the measurement results to the device and the device (1) transmits the said results reaching itself to the remote server (1400). The device (1) is turned off and the method is terminated after the measurement results are transmitted to the remote server.

Figure 4:
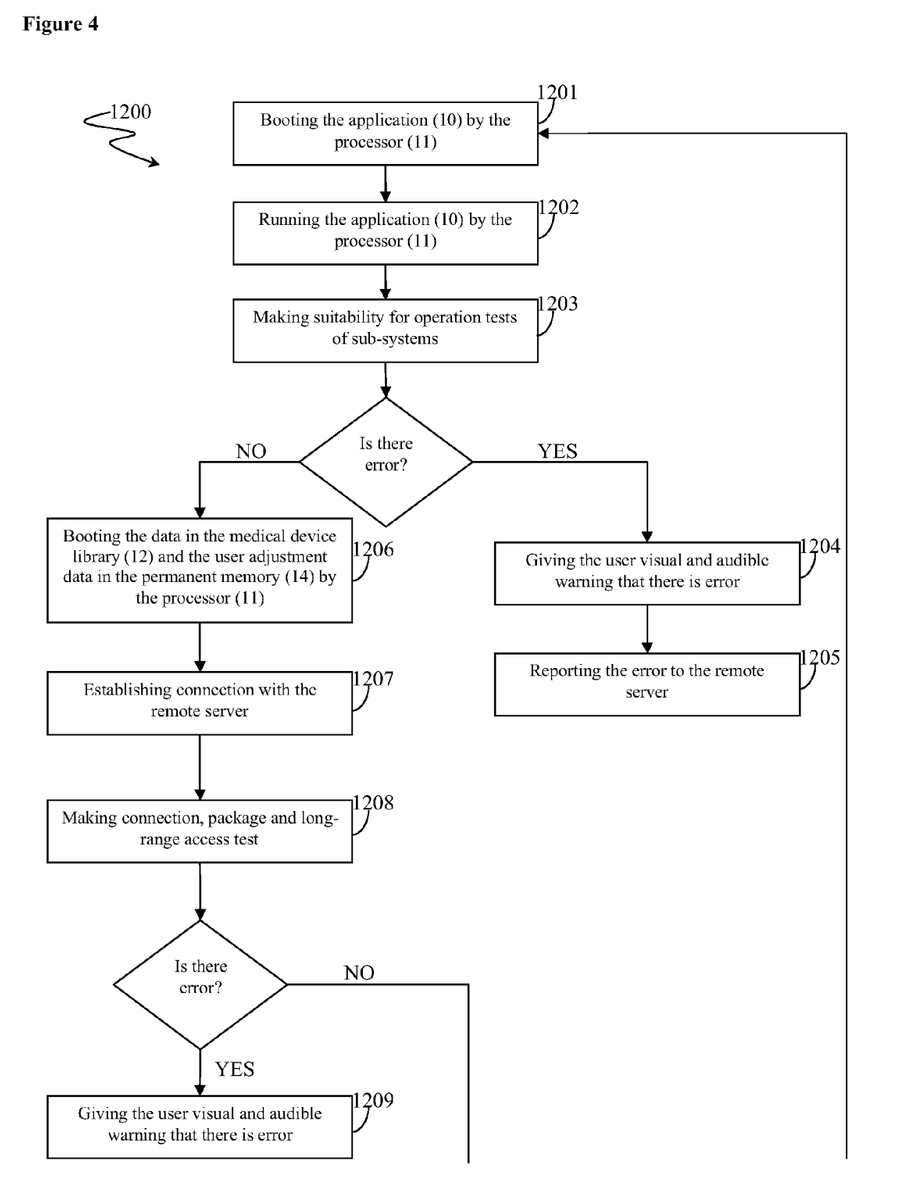
FIG. 4 is a flow diagram regarding step of "making suitability for operation test of device sub-systems and updates thereof" involved in the inventive remote patient management method.
Figure 5:
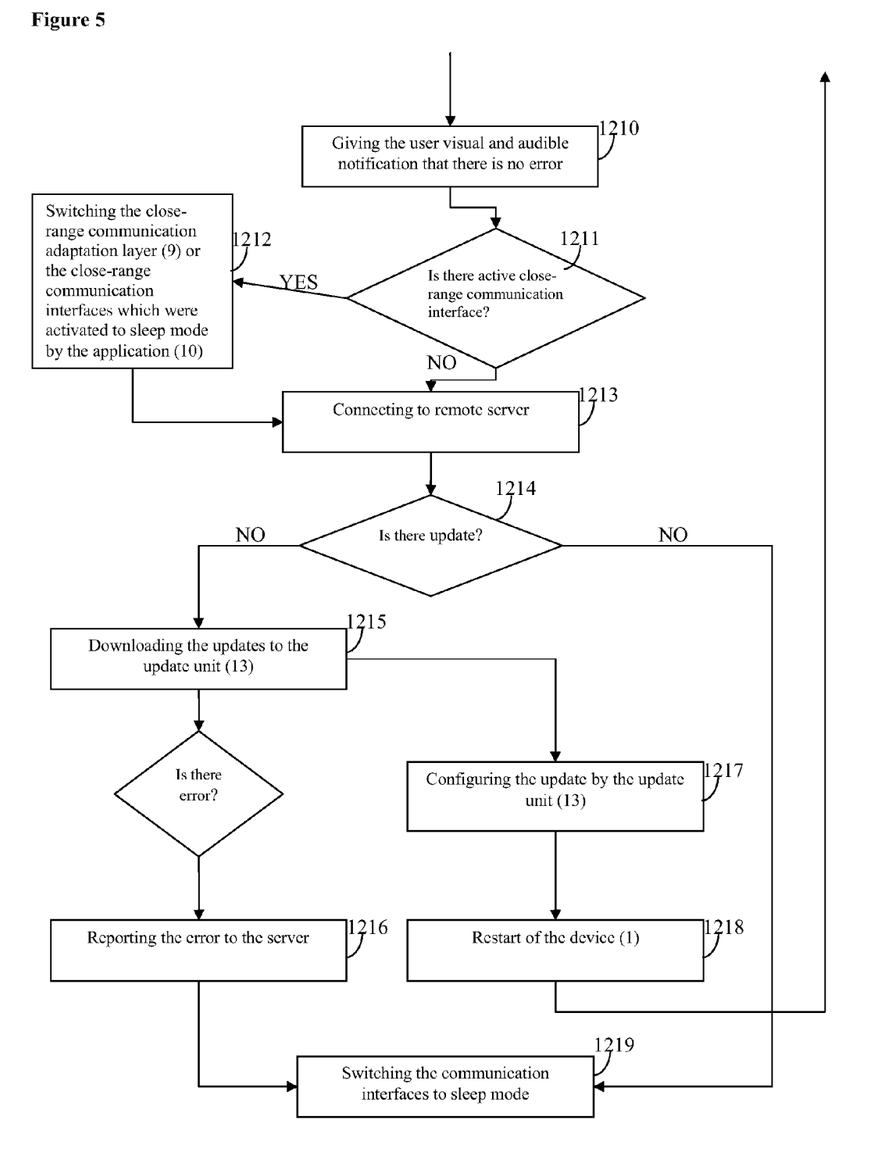
FIG. 5 is continuation of the flow diagram provided in the FIG. 4.

Making suitability for operation test of device (1) sub-systems and updates thereof (1200) comprises sub-steps of:
  booting the application (10), which is located in the non-volatile memory (14), by the processor (11) (1201);
  running the application (10), booting of which is carried out, by the processor (11) (1202);
  making suitability for operation tests of sub-systems by the application (10) (1203);

if it is determined that there is error during tests, giving the patient visual and audible warning that there is error (1204);
reporting the error to the remote server (1205);
if it is determined that there is no error during tests, booting the data in the medical device library (12) and the patient adjustment data in the non-volatile memory (14) by the processor (11) (1206);
establishing connection with the remote server by the application (10) over the long-range communication adaptation layer (9) (1207);
making connection, package and long-range access test by the application (10) (1208);
if it is determined that there is error during connection, package and long-range access tests, giving the patient visual and audible warning that there is error (1209);
if it is determined that there is no error during connection, package and long-range access tests, giving the patient visual and audible notification that there is no error (1210);
controlling by the application (10) whether there is short-range communication adaptation layer (9) or short-range communication interfaces that were activated during error tests (1211);
if it is determined that there is/are short-range communication adaptation layer (9) or short-range communication interfaces which was/were activated during error tests as a result of the control process (1211), switching the short-range communication adaptation layer (9) or the short-range communication interfaces which were activated to sleep mode by the application (10) (1212);
if it is determined that there is/are no short-range communication adaptation layer (9) or short-range communication interfaces which was/were activated during error tests as a result of the control process (1211), connecting to remote server over the short-range communication adaptation layer (9) (1213);
after connecting to the remote server, controlling whether there is update for the application (10) or the medical device library (12) (1214);
if it is determined that there is update after controlling whether there is update at the remote server (1214), downloading the updates to the update unit (13) (1215);
if it is determined that there is error during downloading of the updates to the update unit (13), reporting the error to the server (1216) and switching the communication interfaces to sleep mode (1219);
if it is determined that there is no error during downloading of the updates to the update unit (13), configuring the updates by the update unit (13) (1217); restart of the device (1) (1218); and booting the application (10) located in the non-volatile memory (14) by the processor (11) (1201);
if it is determined that there is no update after controlling whether there is update at the remote server (1214), switching the communication interfaces to sleep mode (1219).

In the inventive method (1000), in order to make suitability for operation test of device (1) sub-systems and updates thereof (1200) firstly the processor (11) carries out booting the application (10) which is located in the non-volatile memory (14) (1201). The application (10) booting of which is carried out is run by the processor (11) (1202). After the application (10) is run, firstly suitability for operation tests of sub-systems—the visual unit (3), the sound generating unit (4), the input unit (5), the short-range communication module (6), the long-range communication module (7)—are made (1203). After the said error tests, if it is determined that there is error in any of the sub-systems the patient is warned via the visual unit (3) by giving out light and the sound generating unit (4) by making a warning sound (1204). Errors, which are detected as a consequence of the error test after the patient is warned, are sent to the remote server by being put into report form (1205). If no error is detected as a consequence of the error tests made by the application (10), booting of the data in the medical device library (12) and the patient adjustment data in the non-volatile memory (14) is carried out by the processor (11) (1206). After the booting process (1206) is performed, connection is established with the remote server by the long-range communication adaptation layer (9) activating at least one of the long-range communication interfaces in the long-range communication module (7) (1207). The application (10) makes connection, package and long-range access tests after it is connected to the remote server (1208). If error is detected as a consequence of the test process (1208) performed by the application (10), the patient is warned that there is error via the visual unit (3) by giving out light and the sound generating unit (4) by making a warning sound (1209). If no error is detected as a consequence of the test process (1208) performed by the application (10), the patient is informed that there is no error via the visual unit (3) by giving out light and the sound generating unit (4) by making a notification sound (1210). After detecting that there is no error and informing the patient (1210), it is controlled whether the short-range communication adaptation layer (9) and/or the short-range communication interfaces located in the short-range communication module (6) were activated during error tests (1211). If it is determined that the short-range communication adaptation layer (9) and/or the short-range communication interfaces located in the short-range communication module (6) were activated as a result of the control process (1211), the activated units are switched to sleep mode (1212). If it is determined that the short-range communication adaptation layer (9) and the short-range communication interfaces located in the short-range communication module (6) were not activated as a result of the control process (1211), connection is established with the remote server by the long-range communication adaptation layer (9) activating at least one of the short-range communication interfaces located in the long-range communication module (7) (1213). After connection is established with the remote server (1213), it is controlled whether there is update for the application (10) or the medical device library (12) (1214). If any update is detected, these updates are downloaded to the update unit (13) (1215). It is controlled whether there is error in the process of downloading update. If it is determined that there is error during downloading of the updates to the update unit (13), the error detected is transmitted to the remote server by being put into report form (1216) and the communication interfaces switched to sleep mode (1219). If it is determined that there is no error after downloading of the updates to the update unit (13), the update is configured by the update unit (13) (1217) and the device (1) restarts (1218). Upon restart of the application and booting of the application (10) located in the non-volatile memory (14) is performed by the processor (11) (1201), the above-stated processes are carried out respectively. If it is determined that there is no update as a consequence of controlling whether there is update at the remote server (1214), the communication interfaces are switched to sleep mode (1219).

Figure 6:
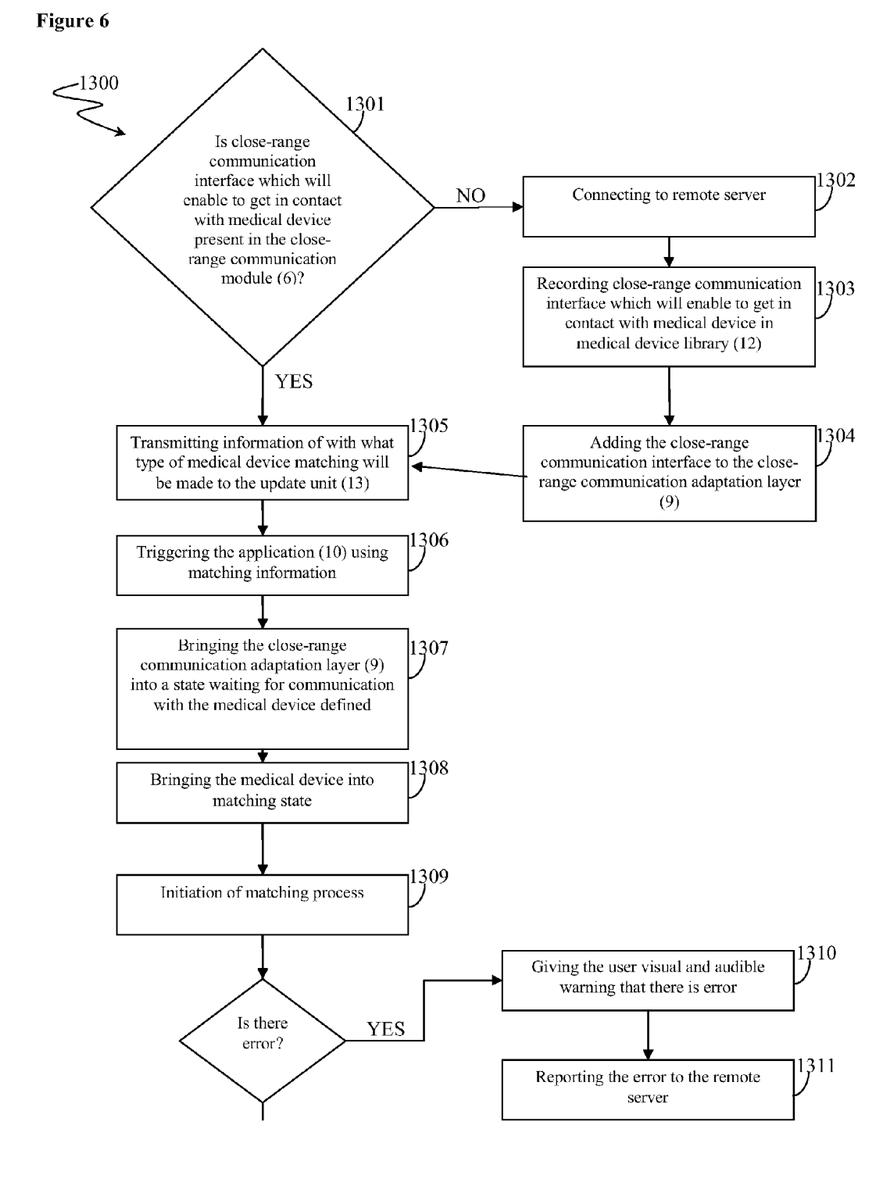
FIG. 6 is a flow diagram regarding step of "matching the device with at least one medical device" involved in the inventive remote patient management method.
Figure 7:
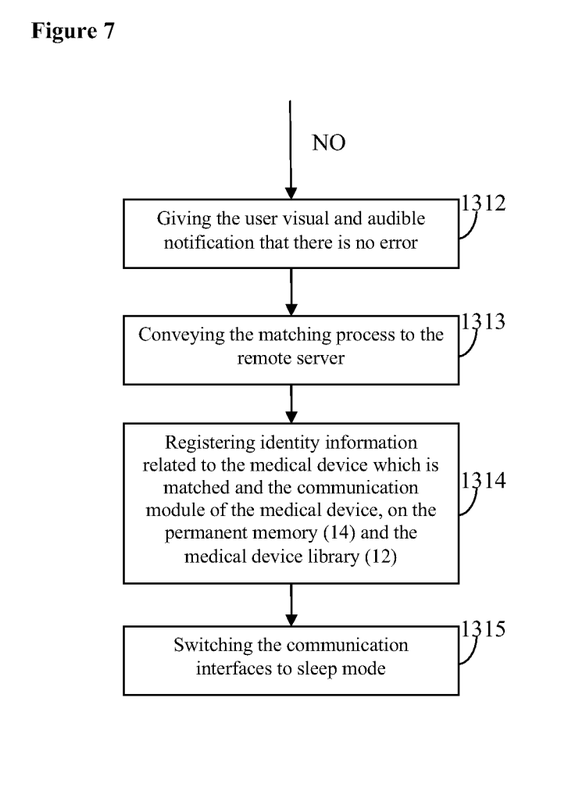
FIG. 7 is continuation of the flow diagram provided in the FIG. 6.

Step of matching the device (1) with at least one medical device (1300) comprises sub-steps of:

controlling whether short-range communication interface which will enable to get in contact with medical device is located in the short-range communication module (6) (1301);

if it is determined that the short-range communication interface which will enable to get in contact with medical device is not located in the short-range communication module (6) as a result of the control process (1301), connecting to remote server over long-range communication adaptation layer (1302);

recording short-range communication interface which will enable to get in contact with medical device in medical device library (12) by the update unit (13) (1303);

adding the short-range communication interface downloaded to the short-range communication adaptation layer (9) (1304);

if it is determined that the short-range communication interface which will enable to get in contact with medical device is located in the short-range communication module (6) as a result of the control process (1301), transmitting information of with what type of medical device matching will be made to the update unit (13) (1305);

triggering the application (10) by the update unit (13) using matching information (1306);

bringing the short-range communication adaptation layer (9) into a state waiting for communication with the medical device defined by the application (10) (1307);

bringing the medical device into matching state (1308);

initiation of matching process by the application (10) (1309);

if it is detected that there is error during the matching process (1309), giving the patient visual and audible warning that there is error (1310) and reporting the error to the remote server (1311);

if it is detected that there is no error during the matching process (1309), giving the patient visual and audible notification that there is no error (1312) and conveying the matching process to the remote server over the short-range communication adaptation layer (9) (1313);

registering identity information related to the medical device which is matched and the communication module of the medical device, on the non-volatile memory (14) and the medical device library (12) (1314);

switching the communication interfaces to sleep mode (1315).

In the inventive method (1000), in order that the device (1) is matched with at least one medical device firstly it is controlled whether the short-range communication interface which will enable to get in contact with medical device is located in the short-range communication module (6) (1301). If it is determined that the short-range communication interface which will enable to get in contact with medical device is not located in the short-range communication module (6) as a result of the control process (1301), connection is established with the remote server upon the short-range communication adaptation layer (9) activates at least one of the long-range communication interfaces in the long-range communication module (7) (1302). After connection is established with the remote server, the update unit (13) records short-range communication interface which will enable to get in contact with medical device in medical device library (12) (1303). The short-range communication interface recorded in the medical device library (12) is added to the short-range communication adaptation layer (9) (1304). If it is determined that the short-range communication interface which will enable to get in contact with medical device is located in the short-range communication module (6) as a result of the control process (1301), information of with what type of medical device matching will be made is transmitted to the update unit (13) (1305). In an embodiment of the invention, information of with what type of medical device matching will be made is transferred to the update unit (13) over the short-range communication adaptation layer (9). In an alternative embodiment of the invention, information of with what type of medical device matching will be made is transferred to the update unit (13) by the user using the input unit (4). Then, the update unit (13) transmits the matching request to the application (10) together with communication protocol information of the medical device to be matched (1306). The application (10) enables the short-range communication adaptation layer (9) to activate the suitable ones of the short-range communication interfaces in the short-range communication module (6) (1307). In this case, the device (1) has now started waiting for the medical device to be matched. Then, the medical device is brought into matching state (1308). After the medical device is brought into matching state, the application (10) initiates the matching process (1309). During the matching process (1309), it is controlled whether there is error. If it is detected that there is error during the matching process (1309), the patient is warned via the visual unit (3) by giving out light and the sound generating unit (4) by making a warning sound (1310). Errors, which are detected as a consequence of the error test after the patient is warned, are sent to the remote server by being put into report form (1311). If it is detected that there is no error during the matching process (1309), the patient is notified via the visual unit (3) by giving out light and the sound generating unit (4) by making a notification sound that there is no error (1312). After the patient is informed (1312), the matching process is notified to the remote server using at least one of the long-range communication interfaces (1313). Then, the identity information related to the medical device which is matched and the medical device communication protocol are registered in the non-volatile memory (14) and the medical device library (12) (1314) and the communication interfaces are switched to sleep mode (1315).

Figure 8:
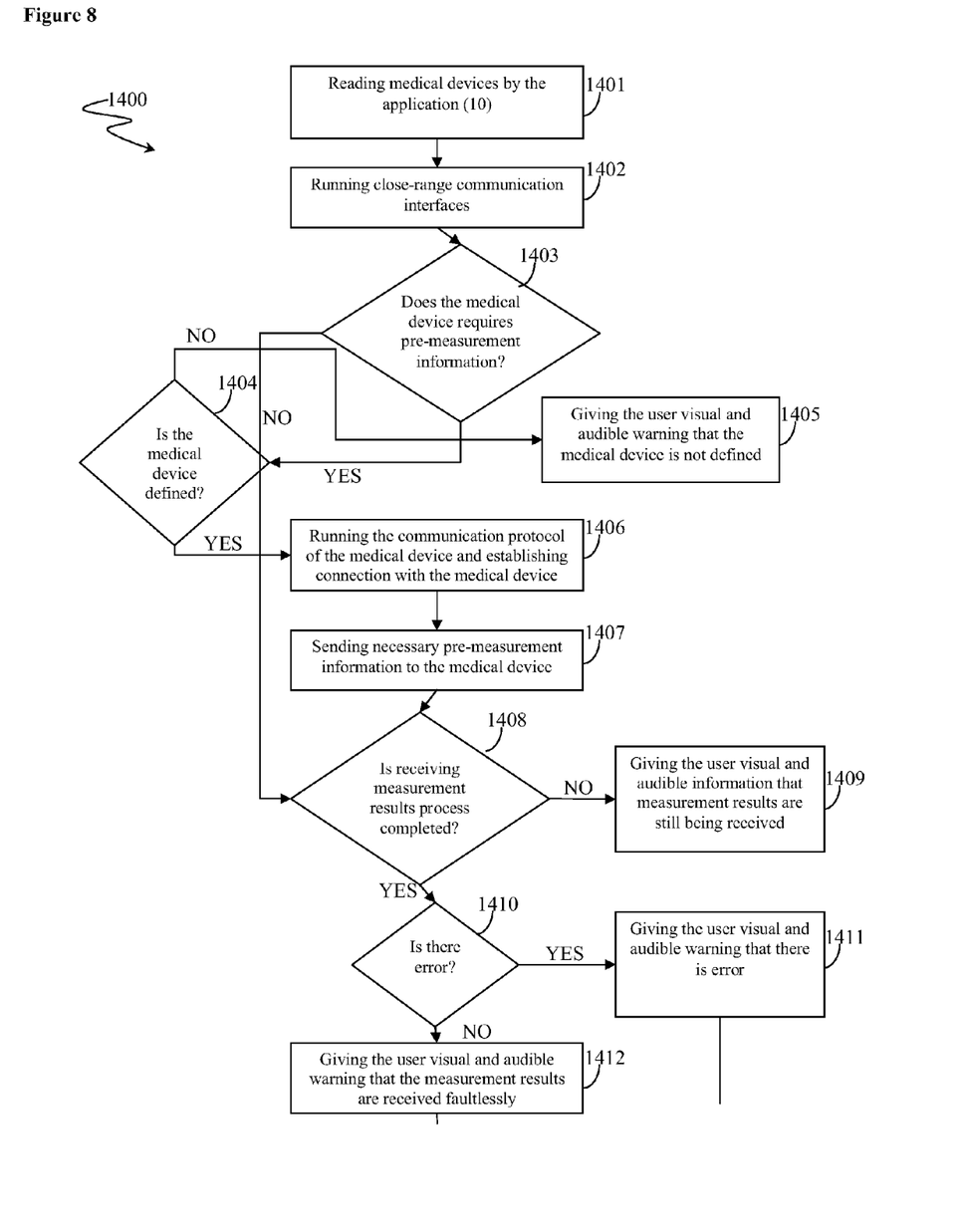
FIG. 8 is a flow diagram regarding step of "obtaining results of measurements from the medical device and transmitting them to a remote server" involved in the inventive remote patient management method.
Figure 9:
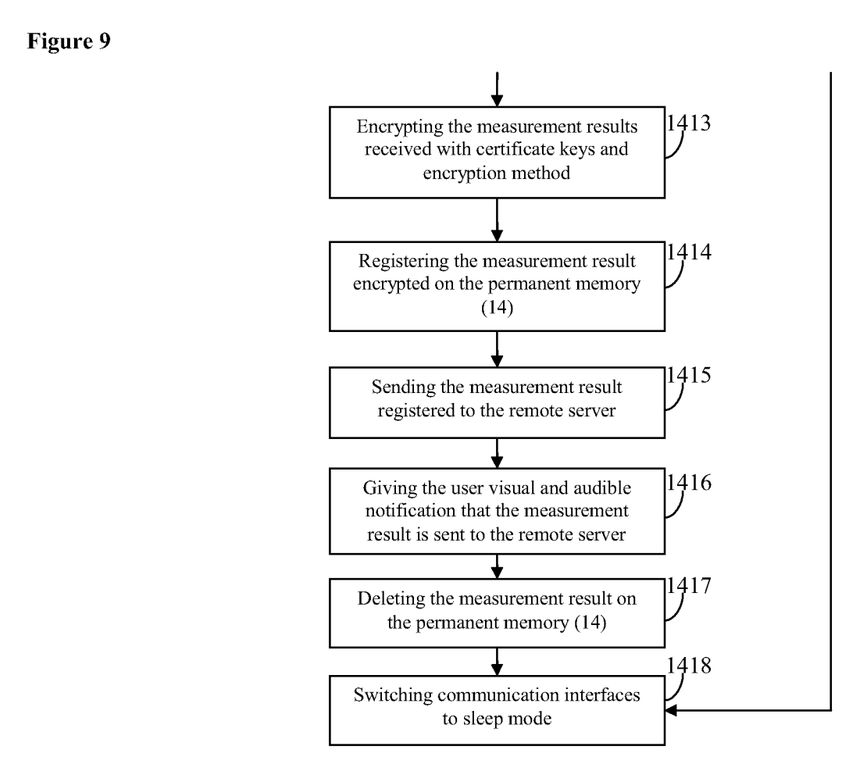
FIG. 9 is continuation of the flow diagram provided in the FIG. 8.

Step of obtaining results of measurements from the medical device and transmitting them to a remote server (1400) comprises sub-steps of:

reading medical devices, which are defined in the medical device library (12) previously, by the application (10) (1401);

running short-range communication interfaces on the short-range communication adaptation layer (9) (1402);

controlling whether medical device which will make measurement requires pre-measurement information such as calibration, time in order to start measuring (1403);

if it is determined that medical device which will make measurement requires pre-measurement information such as calibration, time in order to start measuring after the controlling process (1403), controlling whether the medical device is previously defined (1404);

if it is determined that the medical device is not previously defined after the controlling process (1403), giving the patient visual and audible warning that the medical device is not defined (1405);

if it is determined that the medical device is previously defined as a consequence of the controlling process (1404), running the communication protocol of the medical device and establishing connection with the medical device (1406);

sending necessary pre-measurement information from the medical device library (12) to the medical device (1407);

controlling whether process of receiving measurement results is completed (1408);

if it is determined that process of receiving measurement results is not completed as a consequence of the controlling process (1408), giving the patient visual and audible information that measurement results are still being received (1409);

if it is determined that process of receiving measurement results is completed as a consequence of the controlling process (1408), controlling whether there is error in receiving measurement results (1410);

if it is determined that there is error in receiving measurement results as a consequence of the controlling process (1410), giving the patient visual and audible warning that there is error (1411) and switching the communication interfaces to sleep mode (1418);

if it is determined that there is no error in receiving measurement results as a consequence of the controlling process (1410), giving the patient visual and audible warning that the measurement results are received faultlessly (1412);

encrypting the measurement results received with certificate keys and encryption method (1413);

registering the measurement result encrypted on the non-volatile memory (14) (1414);

sending the measurement result registered to the remote server by means of communication interface over the long-range communication adaptation layer (9) (1415);

giving the patient visual and audible notification that the measurement result is sent to the remote server (1416);

deleting the measurement result on the non-volatile memory (14) after it is sent to the remote server (1417); and switching communication interfaces to sleep mode (1418).

In the inventive method (1000), in order to obtain results of measurements from the medical device and transmit them to a remote server (1400) firstly the application (10) reads medical devices which are defined in the medical device library (12) (1401). Then, the short-range communication adaptation layer (9) activates at least one of the short-range communication interfaces in the short-range communication module (6) (1402). It is controlled whether the medical device which will make measurement requires pre-measurement information such as calibration, time in order to start measuring (1403). If it is determined that the medical device which will make measurement requires pre-measurement information, it is controlled whether the said medical device is previously defined (1404). If the medical device is not previously defined, the patient is warned via the visual unit (3) by giving out light and the sound generating unit (4) by making a warning sound that the medical device is not previously defined (1405). If it is determined that the medical device is previously defined, the communication protocol of the medical device is run and connection is established with the medical device (1406), and pre-measurement information required by the medical device are sent to the medical device defined (1407). Then, it is waited for transmission of the measurement result from the medical device to the device (1). It is controlled whether the process of receiving measurement results are completed at pre-determined intervals (1408). If it is determined that process of receiving measurement results is not completed as a consequence of the controlling process (1408), the patient is informed via the visual unit (3) by giving out light and the sound generating unit (4) by making a notification sound that it is continued to receive the measurement results (1409). If it is determined that receiving measurement results is completed as a consequence of the controlling process (1408), it is controlled whether there is error in receiving measurement results (1410). If it is determined that there is error in receiving measurement results as a consequence of the controlling process (1410), the patient is warned via the visual unit (3) by giving out light and the sound generating unit (4) by making a warning sound that the measurement results have been received incorrectly (1411) and the communication interfaces are switched to sleep mode (1418). If it is determined that there is no error in receiving measurement results as a consequence of the controlling process (1410), the patient is informed via the visual unit (3) by giving out light and the sound generating unit (4) by making a notification sound that the measurement results have been received successfully (1412). The measurement results which have been received successfully are encrypted with certificate keys and encryption method (1413). In the preferred embodiment of the invention, encryption process is realized by reading the personalized digital security certificate on the SIM. The measurement results encrypted are registered on the non-volatile memory (14) in the form of "not sent yet" (1414). The measurement results registered are sent to the remote server by means of communication interfaces over the long-range communication adaptation layer (9) (1415). After the measurement results are sent to the remote server, the patient is informed via the visual unit (3) by giving out light and the sound generating unit (4) by making a warning sound that the measurement results have been sent to the remote server successfully (1416). Lastly, the measurement results which have been registered on the non-volatile memory (14) in the form of "not sent yet" previously are deleted from the non-volatile memory (14) and the communication interfaces are switched to sleep mode (1418).

Via the short-range communication interfaces that it contains on thereof, the inventive remote patient management device (1) can manage medical devices defined by establishing a connection with them; provide information such as time, calibration, etc. which are required in order that medical devices operate; read measurement results which are made by medical devices defined; and transmits the said measurement results to remote servers via long-range communication interfaces using secure communication methods by enabling to determine the patient's identity.

With the inventive remote patient management device (1): identification of medical measurement devices to each other, carrying out security matches, managing medical measurement devices and reading measurement results are performed with minimum patient interaction possible Security definitions required for carrying out communication with medical devices can be carried out both over the remote patient management device (1) and with remote access, and both by the patient and technical assistance personnel.

It is possible to develop various embodiments of the inventive remote patient management device (1) and method (1000), it cannot be limited to examples disclosed herein and it is essentially according to claims.

The invention claimed is:

1. A remote patient management device (1), which is used by a patient, comprising a body (2);

a plurality of visual units (3) which are located on the body (2) and enable to inform and warn the patient visually;

at least one sound generating unit (4) which is located on the body (2) and enables to warn and inform the patient vocally;

at least one input unit (5) which is located on the body (2) and enables the patient to carry out input processes;

at least one short-range communication module (6) which is located in the body (2) and comprises at least one interface enabling contact with devices that are present at short-range including medical devices that will make tests of the patient;

at least one long-range communication module (7) which is located in the body (2) and comprises at least one interface enabling contact with remote servers including transmitting test measurement results of the patient to healthcare centers;

at least one control module (8) which enables the visual units (3), the sound generating unit (4) and the input unit (5) to fulfill their duties and to carry out short communication by means of the short-range communication module (6) and remote communication by means of the long-range communication module (7);

characterized by at least two adaptation layers (9) which enable the control module (8) to interact with the short-range communication module (6) and the long-range communication module (7) in an isolated manner.

2. A remote patient management device (1) according to claim 1, characterized by the adaptation layers (9) which presents a standard set of functions, that is necessary for getting in contact with medical devices and remote servers, to the control module (8).

3. A remote patient management device (1) according to claim 1, characterized by the control module (8) having:
at least one application (10) which controls services that enable remote management of the device (1) and updates, and all components;
at least one processor (11) which enables running an application (10);
at least one medical device library (12) in which identity information relating to the medical devices connected, treatment information and necessary operating information are included;
at least one update unit (13) which enables controlling retrieval of information relating to the application (10) or the medical devices connected from the remote servers; and
at least one non-volatile memory (14) in which the application (10) and the medical device library (12) are kept confidential.

4. A remote patient management device (1) according to claim 1, characterized by the input unit (5) which is a keypad.

5. A remote patient management device (1) according to claim 1, characterized by the input unit (5) which is a touch screen.

6. A remote patient management device (1) according to claim 1, characterized by the short-range communication module (6) which has a bluetooth communication interface that is defined by IEEE 802.15.1 standard.

7. A remote patient management device (1) according to claim 1, characterized by the short-range communication module (6) which has a wireless personal networks communication interface that is defined by IEEE 802.15.4 standard.

8. A remote patient management device (1) according to claim 1, characterized by the short-range communication module (6) which has a Wireless Fidelity (Wi-Fi) communication interface that is defined by IEEE 802.11 series.

9. A remote patient management device (1) according to claim 1, characterized by the short-range communication module (6) which has an infrared communication interface.

10. A remote patient management device (1) according to claim 1, characterized by the short-range communication module (6) which has a wire serial communication interface.

11. A remote patient management device (1) according to claim 1, characterized by the long-range communication module (7) which has an interface of a global system for mobile communications.

12. A remote patient management device (1) according to claim 1, characterized by the long-range communication module (7) which has an Ethernet communication interface.

13. A remote patient management device (1) according to claim 1, characterized by the long-range communication module (7) which has a Wireless Fidelity communication interface.

14. A remote patient management device (1) according to claim 1, characterized by at least one subscriber identity module which enables sending the measurement results that are received from the medical devices to the remote servers by being encrypted with certificate keys and encryption methods.

15. A remote patient management method (1000) enabling people with chronic diseases to make their tests on a regular basis and transmission of test measurement values to healthcare personnel reliably essentially comprising the steps of:
turning on a device (1) (1100);
determining suitability of the device for operation by testing of device (1) sub-systems and making updates thereof (1200);
matching the device (1) with at least one medical device (1300);
obtaining results of measurements from the medical device and transmitting the results to a remote server (1400); and
turning off the device (1) (1500), characterized by the step of determining suitability of the device for operation having the sub-steps of:
booting an application (10), which is located in a non-volatile memory (14), by a processor (11) (1201);
running the application (10) booting of which is carried out, by the processor (11) (1202);
testing of the sub-systems by the application (10) (1203);
if it is determined that there is an error during tests, giving a patient a visual and audible warning that there is the error (1204);
reporting the error to the remote server (1205);
if it is determined that there is no error during tests, booting a data in a medical device library (12) and a patient adjustment data in the non-volatile memory (14) by the processor (11) (1206);
establishing a connection with the remote server by the application (10) over a long-range communication adaptation layer (9) (1207);
making connection, package and long-range access tests by the application (10) (1208);
if it is determined that there is an error during the connection, package and long-range access tests, giving the patient the visual and audible warning that there is the error (1209);
if it is determined that there is no error during the connection, package and long-range access tests, giving the patient a visual and audible notification that there is no error (1210);
controlling by the application (10) whether there is a short-range communication adaptation layer (9) or short-range communication interfaces that were activated during error tests (1211);
if it is determined that there is/are the short-range communication adaptation layer (9) or the short-range communication interfaces which was/were activated during error tests as a result of the control process (1211), switching the short-range communication adaptation layer (9) or the short-range communication interfaces which were activated to a sleep mode by the application (10) (1212);

if it is determined that there is/are no short-range communication adaptation layer (9) or short-range communication interfaces which was/were activated during error tests as a result of the control process (1211), connecting to the remote server over the short-range communication adaptation layer (9) (1213);

after connecting to the remote server, controlling whether there is an update for the application (10) or the medical device library (12) (1214);

if it is determined that there is one or more updates after controlling whether there is an update at the remote server (1214), downloading the updates to an update unit (13) (1215);

if it is determined that there is an error during downloading of the updates to the update unit (13), reporting the error to the server (1216) and switching the communication interfaces to sleep mode (1219);

if it is determined that there is no error during downloading of the updates to the update unit (13), configuring the updates by the update unit (13) (1217); restarting of the device (1) (1218); and booting of the application (10) located in the non-volatile memory (14) by the processor (11) (1201);

if it is determined that there is no update after controlling whether there is the update at the remote server (1214), switching the communication interfaces to sleep mode (1219).

16. A remote patient management method (1000) according to claim 15, characterized by the step of matching the device (1) with at least one medical device (1300) having the sub-steps of:

controlling whether a short-range communication interface which will enable getting in contact with the medical device is located in a short-range communication module (6) (1301);

if it is determined that the short-range communication interface which will enable getting in contact with the medical device is not located in the short-range communication module (6) as a result of the control process (1301), connecting to the remote server over the long-range communication adaptation layer (1302);

recording the short-range communication interface which will enable getting in contact with the medical device in the medical device library (12) by the update unit (13) (1303);

adding the short-range communication interface downloaded to the short-range communication adaptation layer (9) (1304);

if it is determined that the short-range communication interface which will enable getting in contact with the medical device is located in the short-range communication module (6) as a result of the control process (1301), transmitting information of with what type of medical device matching will be made to the update unit (13) (1305);

triggering the application (10) by the update unit (13) using matching information (1306);

bringing the short-range communication adaptation layer (9) into a state waiting for communication with the medical device defined by the application (10) (1307);

bringing the medical device into a matching state (1308);

initiation of a matching process by the application (10) (1309);

if it is detected that there is an error during the matching process (1309), giving the patient the visual and audible warning that there is the error (1310) and reporting the error to the remote server (1311);

if it is detected that there is no error during the matching process (1309), giving the patient the visual and audible notification that there is no error (1312) and conveying the matching process to the remote server over the short-range communication adaptation layer (9) (1313);

registering an identity information related to the medical device which is matched and the communication module of the medical device, on the non-volatile memory (14) and the medical device library (12) (1314);

switching the communication interfaces to the sleep mode (1315).

17. A remote patient management method (1000) enabling people with chronic diseases to make their tests on a regular basis and transmission of test measurement values to healthcare personnel reliably essentially comprising the steps of:

turning on a device (1) (1100);

determining suitability of the device for operation by testing of device (1) sub-systems and making updates thereof (1200);

matching the device (1) with at least one medical device (1300);

obtaining results of measurements from the medical device and transmitting the results to a remote server (1400); and turning off the device (1) (1500), characterized by the step of matching the device (1) with at least one medical device (1300) having the sub-steps of:

controlling whether a short-range communication interface which will enable getting in contact with the medical device is located in a short-range communication module (6) (1301);

if it is determined that the short-range communication interface which will enable getting in contact with the medical device is not located in the short-range communication module (6) as a result of the control process (1301), connecting to the remote server over a long-range communication adaptation layer (1302);

recording the short-range communication interface which will enable getting in contact with the medical device in a medical device library (12) by an update unit (13) (1303);

adding the short-range communication interface downloaded to a short-range communication adaptation layer (9) (1304);

if it is determined that the short-range communication interface which will enable getting in contact with the medical device is located in the short-range communication module (6) as a result of the control process (1301), transmitting information of with what type of medical device matching will be made to the update unit (13) (1305);

triggering an application (10) by the update unit (13) using matching information (1306);

bringing the short-range communication adaptation layer (9) into a state waiting for communication with the medical device defined by the application (10) (1307);

bringing the medical device into a matching state (1308);

initiation of a matching process by the application (10) (1309);

if it is detected that there is an error during the matching process (1309), giving the patient a visual and audible warning that there is the error (1310) and reporting the error to the remote server (1311);

if it is detected that there is no error during the matching process (1309), giving the patient a visual and audible notification that there is no error (1312) and conveying the matching process to the remote server over the short-range communication adaptation layer (9) (1313);

registering an identity information related to the medical device which is matched and the communication module of the medical device, on a non-volatile memory (14) and the medical device library (12) (1314);

switching the communication interfaces to a sleep mode (1315).

18. A remote patient management method (1000) enabling people with chronic diseases to make their tests on a regular basis and transmission of test measurement values to healthcare personnel reliably essentially comprising the steps of:

turning on a device (1) (1100);

determining suitability of the device for operation by testing of device (1) sub-systems and making updates thereof (1200);

matching the device (1) with at least one medical device (1300);

obtaining results of measurements from the medical device and transmitting the results to a remote server (1400); and turning off the device (1) (1500), characterized by the step of obtaining results of measurements from the medical device and transmitting the results to a remote server (1400) having the sub-steps of:

reading one or more medical devices, which are defined in a medical device library (12) previously, by an application (10) (1401);

running a short-range communication interfaces- on a short-range communication adaptation layer (9) (1402);

controlling whether the medical device which will make measurement requires pre-measurement information including calibration, time in order to start measuring (1403);

if it is determined that the medical device which will make measurement requires pre-measurement information including calibration, time in order to start measuring after the controlling process (1403), controlling whether the medical device is previously defined (1404);

if it is determined that the medical device is not previously defined after the controlling process (1403), giving the patient a visual and audible warning that the medical device is not defined (1405);

if it is determined that the medical device is previously defined as a consequence of the controlling process (1404), running a communication protocol of the medical device and establishing a connection with the medical device (1406);

sending necessary pre-measurement information from the medical device library (12) to the medical device (1407);

controlling whether the process of receiving measurement results is completed (1408);

if it is determined that the process of receiving measurement results is not completed as a consequence of the controlling process (1408), giving the patient visual and audible information that measurement results are still being received (1409);

if it is determined that the process of receiving measurement results is completed as a consequence of the controlling process (1408), controlling whether there is an error in receiving measurement results (1410);

if it is determined that there is an error in receiving measurement results as a consequence of the controlling process (1410), giving the patient a visual and audible warning that there is the error (1411) and switching the communication interfaces- to a sleep mode (1418);

if it is determined that there is no error in receiving measurement results as a consequence of the controlling process (1410), giving the patient a visual and audible warning that the measurement results are received faultlessly (1412);

encrypting the measurement results received with certificate keys and an encryption method (1413);

registering the measurement results encrypted on a non-volatile memory (14) (1414);

sending the measurement results registered to the remote server by means of a communication interface over a long-range communication adaptation layer (9) (1415);

giving the patient a visual and audible notification that the measurement results are sent to the remote server (1416);

deleting the measurement results on the non-volatile memory (14) after the results are sent to the remote server (1417); and switching the communication interfaces to sleep mode (1418).

* * * * *